US011648440B2

(12) United States Patent
Kanuparthi et al.

(10) Patent No.: US 11,648,440 B2
(45) Date of Patent: May 16, 2023

(54) SYSTEM AND NON-INTRUSIVE METHOD FOR EXERCISE POSTURE DETECTION

(71) Applicant: WELLNESYS INC., Suwanee, GA (US)

(72) Inventors: Pranav Kanuparthi, Bangalore (IN); Muralidhar Somisetty, Bangalore (IN); Sankar Dasiga, Bangalore (IN)

(73) Assignee: WELLNESYS INC., Suwanee, GA (US)

( * ) Notice: Subject to any disclaimer, the term of this patent is extended or adjusted under 35 U.S.C. 154(b) by 471 days.

(21) Appl. No.: 16/724,402

(22) Filed: Dec. 23, 2019

(65) Prior Publication Data
US 2020/0254299 A1 Aug. 13, 2020

(30) Foreign Application Priority Data
Feb. 11, 2019 (IN) .............................. 201941005350

(51) Int. Cl.
*A63B 21/00* (2006.01)
*A63B 24/00* (2006.01)
(Continued)

(52) U.S. Cl.
CPC ........ *A63B 21/4037* (2015.10); *A61B 5/1116* (2013.01); *A61B 5/486* (2013.01); *A61B 5/681* (2013.01); *A63B 24/0062* (2013.01); *A63B 2024/0065* (2013.01); *A63B 2024/0068* (2013.01); *A63B 2024/0071* (2013.01)

(58) Field of Classification Search
CPC .... A63B 2071/0622; A63B 2071/0663; A63B 2024/0071; A63B 2024/0012; A63B 2024/0065; A63B 2024/0068; A63B 24/0006; A63B 24/0062; A63B 21/4037;
(Continued)

(56) References Cited

U.S. PATENT DOCUMENTS 9,586,120 B1 * 3/2017 Sotelo ................ A63B 71/0669
10,642,360 B2 * 5/2020 Mangharam ............ G06F 3/011
(Continued)

OTHER PUBLICATIONS

Gudino, Miguel. "Engineering Resources: Basics of Analog-to-Digital Converters." Apr. 17, 2018. Arrow Electronics. https://www.arrow.com/en/research-and-events/articles/engineering-resource-basics-of-analog-to-digital-converters (Year: 2018).*
(Continued)

*Primary Examiner* — Sundhara M Ganesan
(74) *Attorney, Agent, or Firm* — IPHorizons PLLC; Narendra Reddy Thappeta

(57) ABSTRACT

A system and non-intrusive method for exercise posture detection are provided. The system includes a mat, at least one sensor matrix comprising one or more sensors and configured to generate an electrical signal upon making a contact by the user with the mat, a plurality of sensor lines, a plurality of power lines and a processing subsystem. The processing subsystem includes a data acquisition module configured to extract a first set of data, to extract a second set of data; a data processing module to process the first set of data and the second set of data, to concatenate the first set of data and the second set of data to get a final set of data, to compare the final set of data with a pre-defined set of posture data, to determine the posture of the at least one exercise.

7 Claims, 5 Drawing Sheets

(51) Int. Cl.
*A61B 5/11* (2006.01)
*A61B 5/00* (2006.01)

(58) Field of Classification Search
CPC ....... A61B 5/1116; A61B 5/486; A61B 5/681; A61B 5/1036; A61B 5/6892
See application file for complete search history.

(56) References Cited

U.S. PATENT DOCUMENTS

| | | | | |
|---|---|---|---|---|
| 2015/0113731 | A1* | 4/2015 | Liu | A63B 6/00 |
| | | | | 5/417 |
| 2015/0364059 | A1* | 12/2015 | Marks | A61B 5/486 |
| | | | | 482/9 |
| 2016/0166876 | A1* | 6/2016 | Goh | G16H 20/30 |
| | | | | 482/9 |
| 2017/0080279 | A1* | 3/2017 | Arredondo | A63B 21/4037 |
| 2018/0317813 | A1* | 11/2018 | Hall | A61B 5/7435 |
| 2019/0001213 | A1* | 1/2019 | Merkel | A61B 5/6892 |
| 2020/0215413 | A1* | 7/2020 | DeMarch | G16H 20/30 |
| 2020/0265746 | A1* | 8/2020 | Derwinger | G09B 5/02 |
| 2021/0038121 | A1* | 2/2021 | Somisetty | A61B 5/1071 |

OTHER PUBLICATIONS

Nosonowitz, Danny. "Using an FSR | Force Sensitive Resistor (FSR)" Nov. 25, 2012. Adafruit Learning System. Accessed from archive.org, https://web.archive.org/web/20121125144912/https://learn.adafruit.com/force-sensitive-resistor-fsr/using-an-fsr (Year: 2012).*

* cited by examiner

SYSTEM AND NON-INTRUSIVE METHOD FOR EXERCISE POSTURE DETECTION

PRIORITY CLAIM

The instant patent application is related to and claims priority from the India patent application entitled, "SYSTEM AND NON-INTRUSIVE METHOD FOR EXERCISE POSTURE DETECTION", Serial No.: 201941005350, Filed: 11 Feb. 2019, which is incorporated in its entirety herein.

FIELD OF INVENTION

Embodiments of a present disclosure relate to monitoring an exercise posture of a user, and more particularly to a system and method to monitor an exercise posture of a user based on physiological parameters.

BACKGROUND

Exercise is defined as any activity which requires physical effort and is carried out to sustain or improve one's health and fitness. Furthermore, with the growth in the technology, different approaches are used to enhance the exercise postures of the user.

In one such approach, a posture detection device is coupled to an exercise mat in order to capture a user's performance associated with an exercise performed on the exercise mat and project the same as a graphical illustration on an interface for the user to perform the exercise based on the graphical illustrations provided by the device. However, in such approach, the exercise performance is not monitored by the device, such limitation restricts the user from receiving guidelines for the exercise being performed. Also, the graphical illustrations provided by the device may not generate a reference for the user to mend the postures of the exercise, which makes such an approach less reliable and less efficient.

In another approach, with the growth in the technology, a plurality of sensors in a form of a matrix is fabricated in a certain pattern within an exercise mat which are used to sense a plurality of parameters of a user upon performing an exercise on the exercise mat. Moreover, in such approach, as a size of the matrix associated with the plurality of sensors increases, a large number of outputs are required. Also, as the matrix gets larger, complexity in acquiring output from the plurality of sensors increases exponentially. In addition, usage of the larger size matrix increases sheer complexity in designing and also becomes expensive as larger matrix requires high power supply and a greater number of sensors. Henceforth, such limitation restricts manufacturing of the exercise mat with larger matrix size. Also, in such an approach, the output from each of the plurality of sensors has to be acquired to recognise the posture of the user, thereby enabling all the sensors to be in contact even though the sensors are not in contact with the exercise posture of the user. Such limitation causes the system to consume more power henceforth making such an approach expensive and less reliable.

Hence, there is a need for an improved system and non-intrusive method for exercise posture detection to address the aforementioned issue/s.

BRIEF DESCRIPTION

In accordance with one embodiment of the disclosure, a system to monitor an exercise posture of a user is provided. The system includes a mat communicatively coupled to at least one wearable device worn by the user. The mat is configured to allow the user to perform at least one exercise. The system also includes at least one sensor matrix located on one of a top of the mat and within the mat. Each of the at least one sensor matrix includes one or more sensors, wherein the one or more sensors is configured to generate an electrical signal upon making a contact of at least one part of a body of the user with the mat while performing the at least one exercise on the mat. The system also includes a plurality of sensor lines. The system also includes a plurality of power lines. Further, the plurality of sensor lines and the plurality of power lines are in a pre-defined ratio. The system also includes a processing subsystem electrically coupled to the at least one sensor matrix. The processing subsystem includes a data acquisition module configured to extract a first set of data from at least one of the one or more sensors through corresponding at least one of the plurality of sensor lines at every predefined time interval sequentially. The data acquisition module is also configured to extract a second set of data from the at least one wearable device, wherein the second set of data is a representative of the at least one exercise performed by the user. The processing subsystem also includes a data processing module operatively coupled to the data acquisition module. The data processing module is configured to process the first set of data and the second set of data using a processing technique. The data processing module is also configured to concatenate the first set of data and the second set of data to get a final set of data. The data processing module is also configured to compare the final set of data with a pre-defined set of posture data. The data processing module is also configured to determine the posture of the at least one exercise performed by the user on the mat based on a compared result. The data processing module is also configured to determine strength and flexibility of the user based on the compared result.

In accordance with another embodiment of the invention, a method for monitoring an exercise posture of a user is provided. The method includes generating an electrical signal upon making a contact of at least one part of a body of the user with a mat while performing at least one exercise on the mat. The method also includes extracting a first set of data from at least one of the one or more sensors through corresponding at least one of the plurality of sensor lines at every pre-defined time interval sequentially. The method also includes a second set of data from the at least one wearable device, wherein the second set of data is a representative of the at least one exercise performed by the user. The method also includes processing the first set of data and the second set of data using a processing technique. The method also includes concatenating the first set of data and the second set of data for getting a final set of data. The method also includes comparing the final set of data with a pre-defined set of posture data. The method also includes determining the posture of the at least one exercise performed by the user on the mat based on a compared result.

To further clarify the advantages and features of the present disclosure, a more particular description of the disclosure will follow by reference to specific embodiments thereof, which are illustrated in the appended figures. It is to be appreciated that these figures depict only typical embodiments of the disclosure and are therefore not to be considered limiting in scope. The disclosure will be described and explained with additional specificity and detail with the appended figures.

BRIEF DESCRIPTION OF THE DRAWINGS

The disclosure will be described and explained with additional specificity and detail with the accompanying figures in which.

Figure 1:
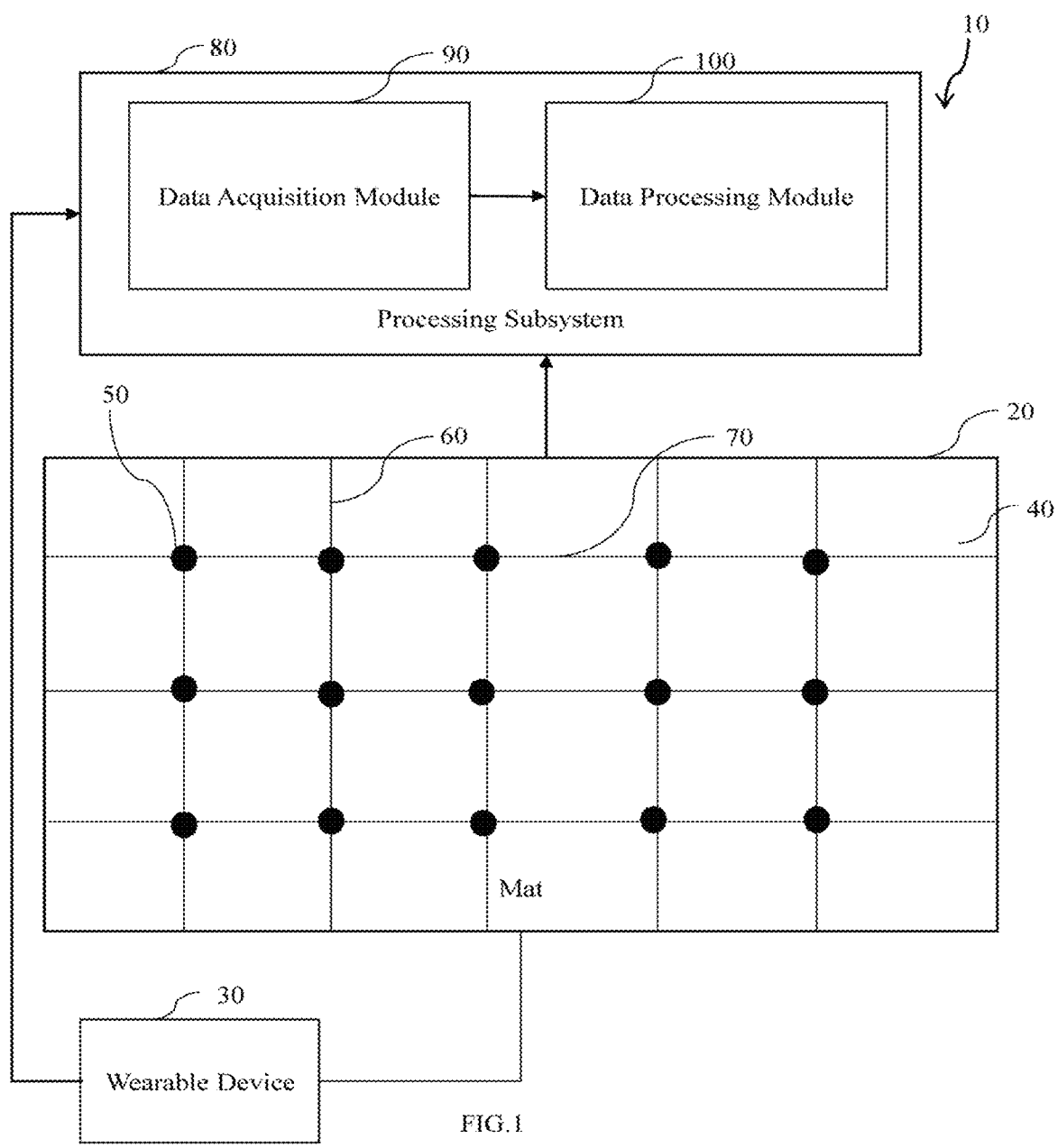
FIG. 1 is a block diagram representation of a system to monitor an exercise posture of a user in accordance with an embodiment of the present disclosure.

Further, those skilled in the art will appreciate that elements in the figures are illustrated for simplicity and may not have necessarily been drawn to scale. Furthermore, in terms of the construction of the device, one or more components of the device may have been represented in the figures by conventional symbols, and the figures may show only those specific details that are pertinent to understanding the embodiments of the present disclosure so as not to obscure the figures with details that will be readily apparent to those skilled in the art having the benefit of the description herein.

DETAILED DESCRIPTION

For the purpose of promoting an understanding of the principles of the disclosure, reference will now be made to the embodiment illustrated in the figures and specific language will be used to describe them. It will nevertheless be understood that no limitation of the scope of the disclosure is thereby intended. Such alterations and further modifications in the illustrated system, and such further applications of the principles of the disclosure as would normally occur to those skilled in the art are to be construed as being within the scope of the present disclosure.

The terms "comprise, comprising", or any other variations thereof, are intended to cover a non-exclusive inclusion, such that a process or method that comprises a list of steps does not include only those steps but may include other steps not expressly listed or inherent to such a process or method. Similarly, one or more devices or sub-systems or elements or structures or components preceded by "com-prises . . . a" does not, without more constraints, preclude the existence of other devices, sub-systems, elements, structures, components, additional devices, additional sub-systems, additional elements, additional structures or additional components. Appearances of the phrase "in an embodiment", "in another embodiment" and similar language throughout this specification may, but does not necessarily, all refer to the same embodiment.

Unless otherwise defined, all technical and scientific terms used herein have the same meaning as commonly understood by those skilled in the art to which this disclosure belongs. The system, methods, and examples provided herein are only illustrative and not intended to be limiting.

In the following specification and the claims, reference will be made to a number of terms, which shall be defined to have the following meanings. The singular forms "a", "an", and "the" include plural references unless the context clearly dictates otherwise.

Embodiments of the present disclosure relate to a system and method to monitor an exercise posture of a user. The system includes a mat communicatively coupled to at least one wearable device worn by the user. The mat is configured to allow the user to perform at least one exercise. The system also includes at least one sensor matrix located on one of a top of the mat and within the mat. Each of the at least one sensor matrix includes one or more sensors, wherein the one or more sensors is configured to generate an electrical signal upon making a contact of at least one part of a body of the user with the mat while performing the at least one exercise on the mat. The system also includes a plurality of sensor lines. The system also includes a plurality of power lines. Further, the plurality of sensor lines and the plurality of power lines are in a pre-defined ratio. The system also includes a processing subsystem electrically coupled to the at least one sensor matrix. The processing subsystem includes a data acquisition module configured to extract a first set of data from at least one of the one or more sensors through corresponding at least one of the plurality of sensor lines at every pre-defined time interval sequentially. The data acquisition module is also configured to extract a second set of data from the at least one wearable device, wherein the second set of data is a representative of the at least one exercise performed by the user. The processing subsystem also includes a data processing module operatively coupled to the data acquisition module. The data processing module is configured to process the first set of data and the second set of data using a processing technique. The data processing module is also configured to concatenate the first set of data and the second set of data to get a final set of data. The data processing module is also configured to compare the final set of data with a pre-defined set of posture data. The data processing module is also configured to determine the posture of the at least one exercise performed by the user on the mat based on a compared result. The data processing module is also configured to determine strength and flexibility of the user based on the compared result.

FIG. 1 is a block diagram representation of a system (10) to monitor an exercise posture of a user in accordance with an embodiment of the present disclosure. as used herein, the term "exercise" is defined as any activity requiring a physical effort which is carried out in order to sustain or improve health and fitness of the user. In one embodiment, the exercise may include at least one of yoga, gym, gymnastic, a Pilates and the like. In one embodiment, the user may be a person who may be learning to perform the exercise. In another embodiment, the user may be the person who may be performing the exercise regularly.

Furthermore, the system (10) includes a mat (20) communicatively coupled to at least one wearable device (10) worn by the user. In one embodiment, the mat (20) may include one of a Pilates mat, a yoga mat, a fitness mat, a wellness mat and the like. In one exemplary embodiment, the wearable device (30) may include one of an implantable, a smartwatch, a smart jewellery, a smart clothing, a head mounted device, and the like. In such embodiment, at least one of a roll, a yaw and a pitch may be used to determine arm joint angles of each arm of the user.

The system (10) also includes at least one sensor matrix (40) located on one of a top of the mat (20) and within the mat (20). Each of the at least one sensor matrix (40) comprises one or more sensors (50). As used herein, the term "sensor matrix" is defined as a group of sensors fabricated together in a certain pattern. The one or more sensors (50) is configured to generate an electrical signal upon making a contact of at least one part of a body of the user with the mat (20) while performing the at least one exercise on the mat (20). In one embodiment, the one or more sensors (50) may be at least one of a pressure sensor, a contact sensor, a touch sensor, a stability sensor, a temperature sensor, a proximity sensor and the like.

The system (10) also includes a plurality of sensor lines (60). In one embodiment, the plurality of sensor lines (60) may be fabricated in a vertical direction. The plurality of sensor lines (60) may be configured to sense or receive an output from the corresponding one or more sensors (50). In one embodiment, an output representative of the electrical signal generated by the one or more sensors (50) may be sensed at every pre-defined interval.

Furthermore, the system (10) includes a plurality of power lines (70). In one embodiment, the plurality of power lines (70) may be configured to supply power to the at least one sensor matrix. Further, the plurality of sensor lines (60) and the plurality of power lines (70) are in a pre-defined ratio. More specifically, number of the plurality of power lines (70) to a number of the plurality of sensor lines (60) may be pre-defined to optimise the monitoring of the exercise posture of the user performed on the mat (20).

In one exemplary embodiment, a junction where at least one of the plurality of sensor lines (60) may meet a corresponding at least one of the plurality of power lines (70) may be treated as a sensor cell. Henceforth, the system (10) may include a plurality of sensor cells (50). In another exemplary embodiment, size of the at least one sensor matrix (40) may be of a dimension of m×n, wherein 'm' may represent the number of the plurality of sensor lines (60) and 'n' may represent the number of the plurality of power lines (70). In such embodiment, at any instant of time 't', only one of the plurality of power lines (70) may be active in order to extract the output from a corresponding at least one of the plurality of sensor lines (60). Also, the sensor matrix (40) may include m×n output lines (not shown in FIG. 1).

The system (10) also includes a processing subsystem (80) electrically coupled to the at least one sensor matrix (40). The processing subsystem (80) includes a data acquisition module (90). The data acquisition module (90) is configured to extract a first set of data from at least one of the one or more sensors (50) through corresponding at least one of the plurality of sensor lines (60) at every pre-defined time interval sequentially. More specifically, an output representative of the electrical signal may be acquired by the data acquisition module (90) from each of the plurality of sensor lines (60) electrically coupled to the corresponding one or more sensors (50). In one specific embodiment, the at least one sensor matrix (40) having the m×n size with 'm' number of the sensor lines (60) and n number of the power lines (70), only one of the 'n' number of the power lines may be active (say, an activated power line be represented as 'i'). More specifically, 'm' number of sensors (50) on the i th row may be active. Henceforth an output from the at least one sensor matrix (40) may be electrical signals generated by the m number of sensors on the i th row.

The data acquisition module (90) is also configured to extract a second set of data from the at least one wearable device (30). The second set of data is a representative of the at least one exercise performed by the user. In one embodiment, the second set of data may be extracted from the at least one wearable device (30) via a communication medium (not shown in FIG. 1). In such embodiment, the communication medium may be a wireless communication medium. In one embodiment, the wireless communication medium may include one of a Wi-Fi™ (wireless fidelity) medium, a Bluetooth™ medium, a Bluetooth™ Low Energy (Bluetooth™ LE or BLE) medium, an LPWAN (low-power wide-area net-work) medium, an Ultra-Wide Band (UWB) medium, a LoRa (Low Range technology) medium, Zigbee™, WLAN (Wireless Local Area Network), a mobile network and the like.

Furthermore, the processing subsystem (80) includes a data processing module (100) operatively coupled to the data acquisition module (90). The data processing module (100) is configured to process the first set of data and the second set of data using a processing technique.

The data processing module (100) is also configured to concatenate the first set of data and the second set of data to get a final set of data. In one embodiment, the final set of data may be in a form off an electrical signal or a value associated with the electrical signal, wherein the electrical signal may be a combination of signals retrieved from the at least one sensor matrix (40) and the at least one wearable device (30). In such embodiment, the value may be a numerical value Furthermore, the data processing module (100) is also configured to compare the final set of data with a pre-defined set of posture data. In one embodiment, the pre-defined set of posture data may be associated with a posture of the at least one exercise which the user may be performing on the mat (20). More specifically, the posture associated with the at least one exercise is performed on the mat by an expert and electrical signal generated by the at least one sensor matrix (40) may be retrieved and stored in a database (not shown in FIG. 1). Further, when the user performs the at least one exercise on the mat (20), the electrical signal associated with the exercise performed by the user generated by the one or more sensors (50) may be compared with the pre-defined set of posture data which may be stored in the database to monitor the accuracy level of the posture of at least one exercise performed by the user.

The data processing module (100) is also configured to determine the posture of the at least one exercise performed by the user on the mat (20) based on a compared result. Referring to the above mentioned embodiment, the compared result may refer to a result obtained upon comparing the final set of data associated with the at least one exercise performed by the user with the pre-defined set of posture data which may be performed by the expert. As used herein, the term "expert" may refer to a person skilled in performing the at least one exercise.

The data processing module (100) is also configured to determine strength and flexibility of the user based on the compared result. In one embodiment, strength and flexibility of the user may be determined based on the electrical signal generated by the one or more sensors (50) when the user performs the at least one exercise on the mat (20). In such embodiment, strength and flexibility of the user may be determined based on the compared result. In one exemplary embodiment, the data processing module (100) may further be configured to generate a fitness score based on the compared result, wherein the fitness score may be associated with at least one of the strength, flexibility and wellness of the user.

In one exemplary embodiment, the data processing module (100) may determine at least one of the posture of the at least one exercise, the strength, the flexibility, weight distribution of the user on the mat (20) while performing the at least one exercise and the like upon using an analysis technique, wherein the analysis technique may be at least one of an artificial intelligence technique and a machine learning technique. As used herein, the term "artificial intelligence technique" is defined as an intelligence demonstrated by a machine which is in contrast with natural intelligence displayed by humans and animals. Also, the term "machine learning" is defined as a scientific study of statistical models used by a computer system to progressively improve performance of the computer system on a specific task. In one embodiment, based on at least one of determined parameters, the processing subsystem (80) may further include a detection module (not shown in FIG. 1) which may be operatively coupled to the data acquisition module (90). The detection module may be configured to detect a height of the user, a weight of the user, an arm length, a leg length and the like. Such determination may further help in determining the posture associated with an upper body and a lower body of the user individually to get more accurate posture.

In one exemplary embodiment, the processing subsystem (80) may further include a representation module (not shown in FIG. 1) operatively coupled to the data processing module (100). The representation module may be configured to represent the posture of the at least one exercise performed by the user in at least one of a two-dimensional image and a three-dimensional image. In one embodiment, the posture of the at least one exercise performed by the user may be represented on a display (not shown in FIG. 1) which may be electrically coupled to the mat (20) and the at least one sensor matrix (40) as the two-dimensional image.

In one exemplary embodiment, the two-dimensional image and the three-dimensional image associated with the posture of the user while performing the at least one exercise may be combined in order to generate a three-dimensional heuristic model of the user which may enable the user for self-learning of the at least one exercise upon implementing the heuristic technique. As used herein, the term "heuristic technique" is defined as a technique of employing a practical method towards self-discovery and self-learning.

In one preferred embodiment, the posture of the at least one exercise performed by the user may be represented to the user through at least one of a Virtual reality (VR) display, an augmented reality (AR) display and a mixed reality display. In such embodiment, the display may be made using a corresponding at least one of a VR display, an AR display and a mixed reality display. In another preferred embodiment, the posture of the at least exercise performed by the user may be represented by a Helio™ display. In such embodiment, the representation may be used by the user in order observe one's own posture and alter the position to a desired or appropriate position in comparison with the pre-defined set of posture data.

In one specific embodiment, the system (10) may be integrated with a voice enabled device (not shown in FIG. 1) which may be configured to assist the user with speech, which may help the user to correct the posture and the angle of the user in real-time.

In one exemplary embodiment, the processing subsystem (80) may further include a posture detection module (not shown in FIG. 1) operatively coupled to the representation module. The posture detection module may be configured to determine the posture of the at least one exercise of the user from at least one of the two-dimensional image and the three-dimensional image using a computer vision technique. The position detection module may also be configured to generate a recommendation associated with the posture of the at least one exercise of the user based on a determined posture. Referring back to the above mentioned embodiment, the user may alter the position of the at least one exercise being performed on the mat (20) based on the recommendation which may be generated by the posture detection module. In one embodiment, the recommendation may be in a form of one of a text notification, a voice notification, a video notification, a multimedia notification and the like.

Furthermore, the system (10) may include a storage device (not shown on FIG. 1) which may be operatively coupled to the processing subsystem (80), wherein the storage device may be configured to store a plurality of details associated with the posture of the user upon performing the at least one exercise on the mat (20).

Figure 2:
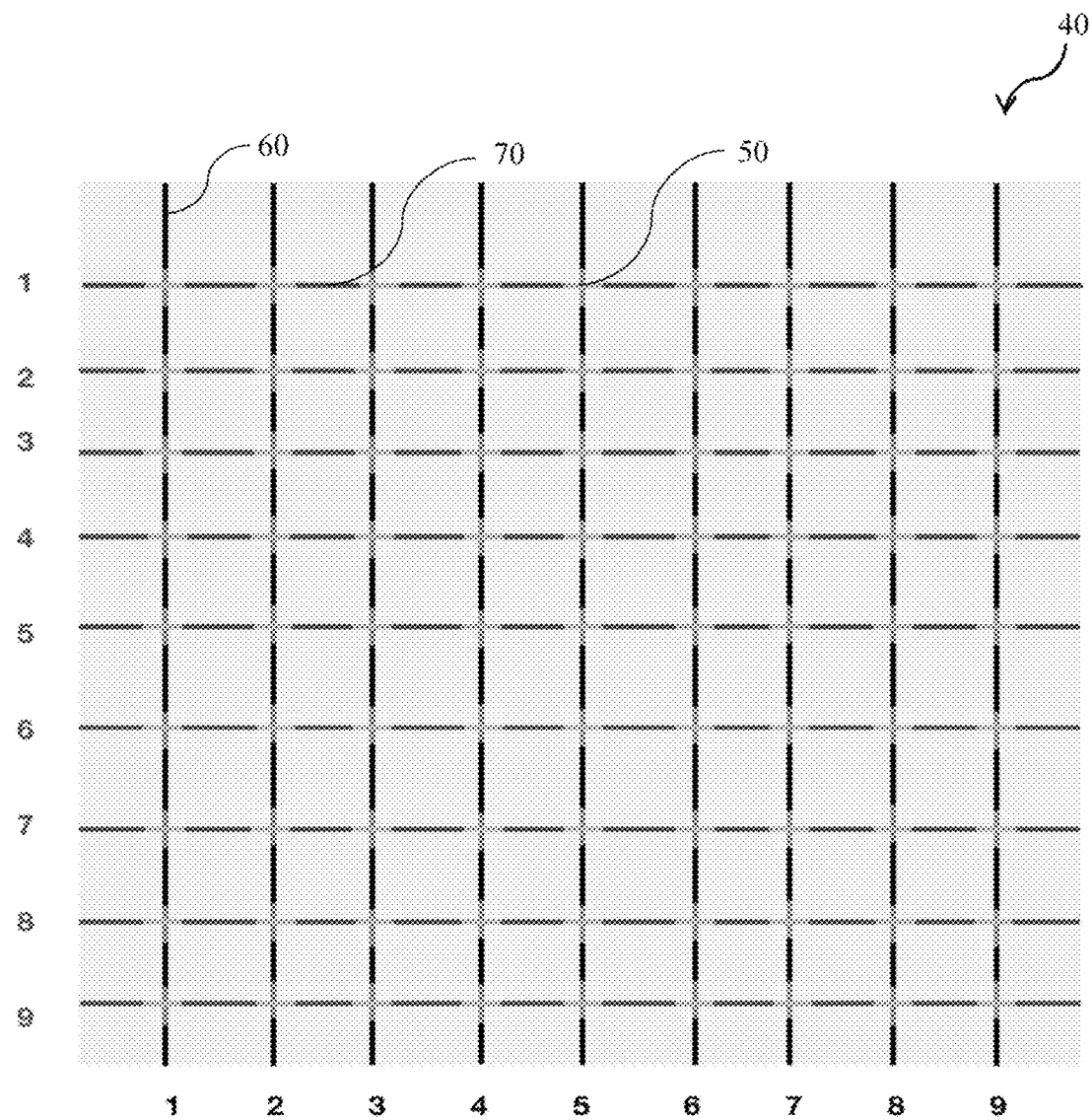
FIG. 2 is a schematic representation of an embodiment of a sensor matrix of FIG. 1 in accordance with an embodiment of the present disclosure.
Figure 3:
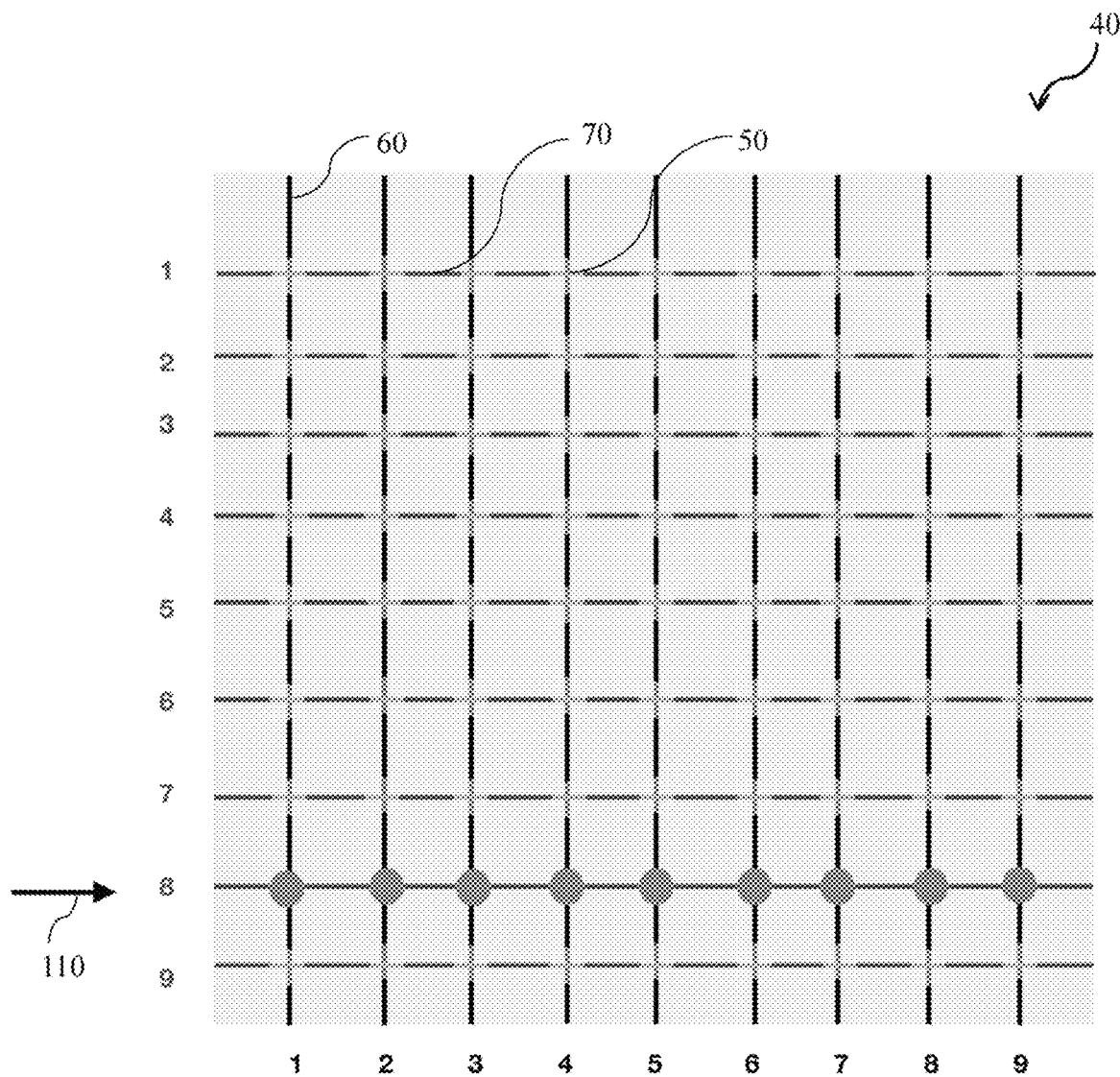
FIG. 3 is schematic representation of another embodiment of a sensor matrix of FIG. 1 in accordance with an embodiment of the present disclosure.

FIG. 2 is a schematic representation of an embodiment of a sensor matrix (40) of FIG. 1 in accordance with an embodiment of the present disclosure. The mat (not shown in FIG. 2) includes the sensor matrix (40). A plurality of vertical lines represents the plurality of sensor lines (60), wherein the plurality of sensor lines (60) is nine in number. Further, a plurality of horizontal lines represents the plurality of power lines (70). The plurality of junctions where the plurality of sensor lines and the corresponding plurality of power lines (70) meet corresponds to the plurality of sensor cells. As the sensor matrix (40) includes nine power lines (70) and nine sensor lines (60), the plurality of output lines (not shown in FIG. 1) is nine in number as only one of the nine power lines are being activated at every pre-defined instant of time, wherein a delay time to activate a succeeding power line (70) is very minimal. For example, an 8th power line (110) of the nine power lines (70) is activated, a plurality of sensors associated with the 8th power line (110) is activated (as shown in FIG. 3).

Figure 4:
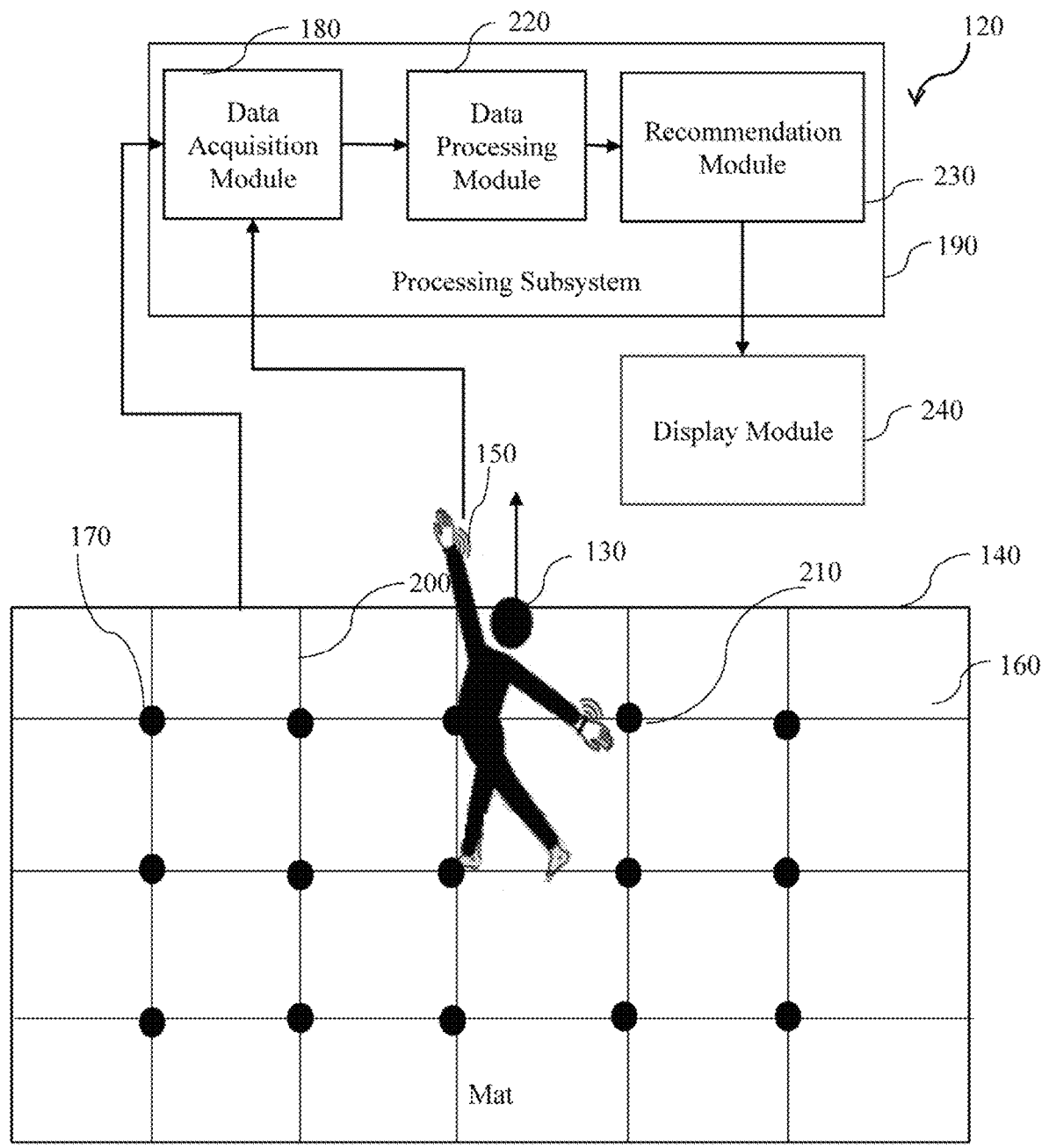
FIG. 4 is an exemplary embodiment representing a system to monitor an exercise posture of a user of FIG. 1 in accordance with an embodiment of the present disclosure.

FIG. 4 is an exemplary embodiment representing a system (120) to monitor an exercise posture of a user (130) of FIG. 1 in accordance with an embodiment of the present disclosure. The system (120) includes a mat (140) communicatively coupled to a wearable smartwatch (150) worn by the user (130), wherein the mat (140) is used by the user (130) to perform an exercise. As the user (130) performs the exercise, a sensor matrix (160) which is fabricated on top portion of the mat (140) comprising a plurality of sensors (170) begins to sense various parameters associated with the exercise such as pressure, weight, distance between user's hands and legs, and the like upon being contacted with a body of the user (130) with the mat (140). Furthermore, a data acquisition module (180) present within a processing subsystem (190) acquires a first set of data from the plurality of sensors (170) via a plurality of output lines (1 not shown in FIG. 4) coupled to a plurality of power lines (200) and a plurality of power lines (210). An output from each of the plurality of output lines is taken sequentially at every pre-defined time interval.

In addition, output from the wearable smartwatch (150) worn by the user (130) is extracted by the data acquisition module (180) as a second set of data. Further, a data processing module (190) operatively coupled to the data acquisition module (220) processes the first set of data and the second set of data and further concatenates the same to get a final set of data which is associated with the exercise performed by the user (130) on the mat (140). The final set of data is compared with a pre-defined set of posture data in order to determine an exact posture of the user (130) while performing the exercise.

Furthermore, the posture determined is represented as a heuristic image for the user (130) to observe and correct the posture if required through a display (240). In a situation when the posture of the user (130) does not match with the pre-defined set of posture data, a recommendation module (230) may generate a recommendation associated with the posture of the exercise of the user (130) based on a determined posture.

Moreover, the mat (140), the sensor matrix (160), the plurality of sensors (170), the plurality of sensor lines (200), the plurality of power lines (210), the processing subsystem (190), the data acquisition module (180) and the data processing module (220) are substantially similar to a mat (20), a sensor matrix (40), a plurality of sensors (50), a plurality of sensor lines (60), a plurality of power lines (70), a processing subsystem (80), a data acquisition module (90) and a data processing module (100) of FIG. 1.

Figure 5:
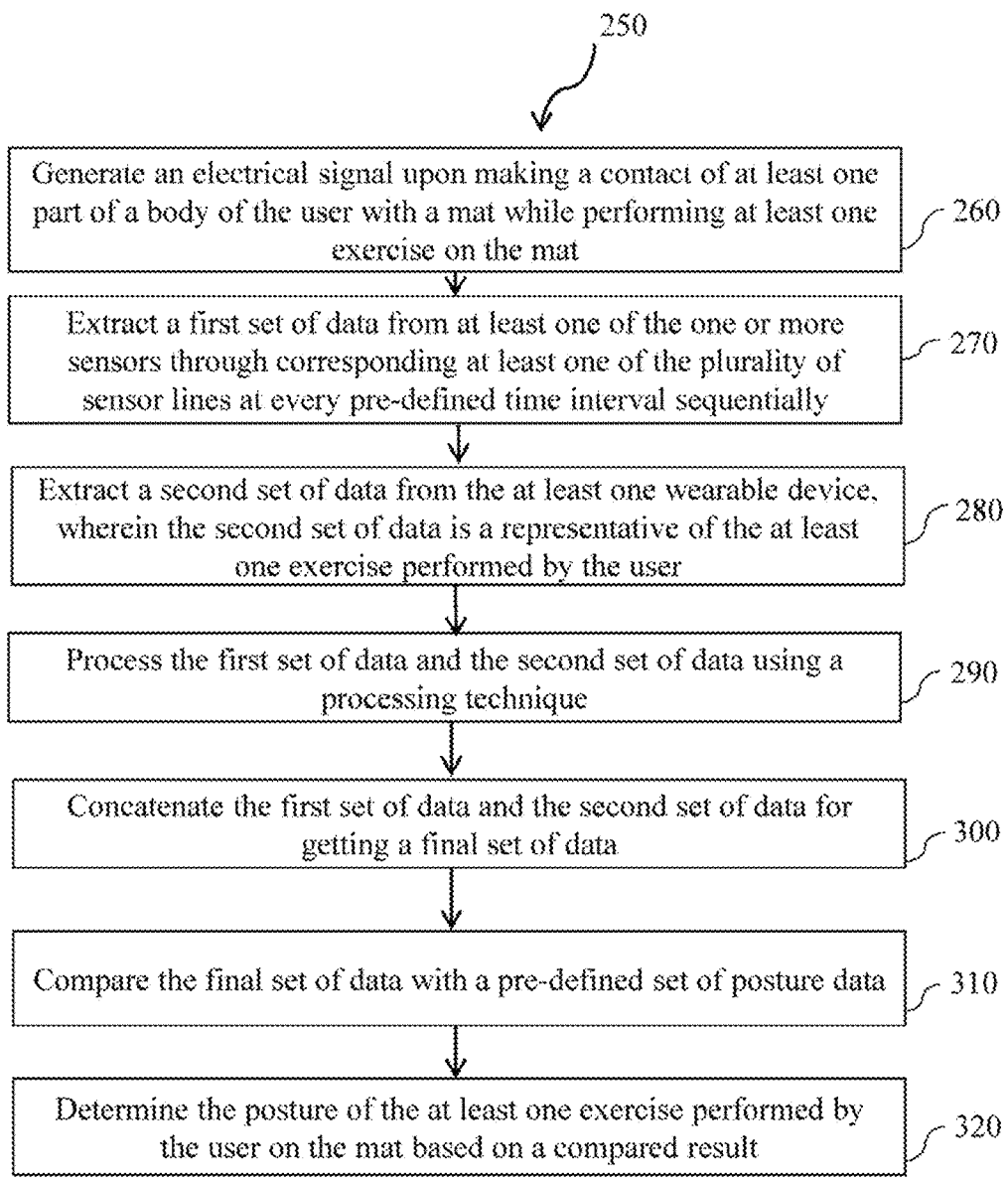
FIG. 5 is a flow chart representing steps involved in a method for monitoring an exercise posture of a user in accordance with an embodiment of the present disclosure.

FIG. 5 is a flow chart representing steps involved in a method (250) for monitoring an exercise posture of a user in accordance with an embodiment of the present disclosure. The method (250) includes generating an electrical signal upon making a contact of at least one part of a body of the user with a mat while performing at least one exercise on the mat in step 260. In one embodiment, generating the electrical signal may include generating the electrical signal by at least one sensor matrix comprising one or more sensors. In one exemplary embodiment, generating the electrical signal may include generating the electrical signal by at least one of a pressure sensor, a contact sensor, a touch sensor, a stability sensor, a temperature sensor, a proximity sensor and the like upon making a contact of at least one part of a body of the user with the mat.

The method (250) also includes extracting a first set of data from at least one of the one or more sensors through corresponding at least one of the plurality of sensor lines at every pre-defined time interval sequentially in step 270. In one embodiment, extracting the first of data may include extracting the first set of data from a data acquisition module. In one exemplary embodiment, extracting the first set of data may include extracting the first set of data by a plurality of output lines associated with a plurality of power lines and a plurality of sensor lines.

The method (250) also includes extracting a second set of data from the at least one wearable device, wherein the second set of data is a representative of the at least one exercise performed by the user in step 280. In one embodiment, extracting the second set of data may include extracting the second set of data by the data acquisition module. In one exemplary embodiment, extracting the second set of data may include extracting the second set of data from the at least one wearable device via a communication medium, wherein the communication medium may include one of a Wi-Fi™ (wireless fidelity) medium, a Bluetooth™ medium, a Bluetooth Low Energy™ (Bluetooth LE or BLE) medium, an LPWAN (low-power wide-area network) medium, an Ultra-Wide Band (UWB) medium, a LoRa (Low Range technology) medium, Zigbee™, WLAN (Wireless Local Area Network), a mobile network, and the like.

Furthermore, the method (250) includes processing the first set of data and the second set of data using a processing technique in step 290. In one embodiment, processing the first set of data and the second set of data may include processing by a data processing module.

The method (250) also includes concatenating the first set of data and the second set of data for getting a final set of data in step 300. In one embodiment, concatenating the first set of data and the second set of data may include concatenating by the data processing module. In one exemplary embodiment, concatenating the first set of data and the second set of data may include concatenating the first set of data and the second set of data for getting a numerical value.

The method (250) also includes comparing the final set of data with a pre-defined set of posture data in step 310. In one embodiment, comparing the final set of data may include comparing the second set of data by the data processing module. In one exemplary embodiment, the method (250) may further include enabling an expert for performing the at least one exercise on the mat. The method (250) may also include extracting the electrical signal from the one or more sensors associated with the mat upon enabling the expert to perform the at least one exercise. The method (250) may further include storing the generated electrical signal as a pre-defined posture data in a database.

Furthermore, the method (250) includes determining the posture of the at least one exercise performed by the user on the mat based on a compared result in step 320. In one embodiment, determining the posture of the at least one exercise may include determining the posture by the data processing module. In one exemplary embodiment, determining the posture may include determining the posture of the at least one exercise performed by the user on mat upon comparing the final set of data with the pre-defined posture data.

In one specific embodiment, the method (250) may further include determining strength and flexibility of the user based on the compared result. In another specific embodiment, the method (250) may further include generating a fitness score based on the compared result, wherein the fitness score may be associated with at least one of the strength, flexibility and wellness of the user. In such embodiment, the method (250) may include determining at least one of the posture of the at least one exercise, the strength, the flexibility, weight distribution of the user on the mat while performing the at least one exercise and the like upon using an analysis technique, wherein the analysis technique may be at least one of an artificial intelligence technique and a machine learning technique. In yet another specific embodiment, the method may further include detecting a height of the user, a weight of the user, an arm length, a leg length and the like. In such embodiment, the method may further include determining the posture associated with an upper body and a lower body of the user individually to get more accurate posture.

In one specific embodiment, the method (250) may further include representing the posture of the at least one exercise performed by the user in at least one of a two-dimensional image and a three-dimensional image. In such embodiment, representing the posture may include representing the posture by a representation module. In one exemplary embodiment, representing the posture may include determining the posture of the at least one exercise of the user from at least one of the two-dimensional image and the three-dimensional image using a computer vision technique. In one embodiment, determining the posture may include determining the posture by a postured detection module. The method may further include generating a recommendation associated with the posture of the at least one exercise of the user based on a determined posture. In one embodiment, generating the recommendation may include generating the recommendation by the posture detection module.

In one specific embodiment, representing the posture may include representing the posture in one of at least one of a virtual reality (VR) display, an augmented reality (AR) display and a mixed reality display.

Various embodiments of the present disclosure enable the system to monitor and guide the user performing an exercise in real time by the user expert which helps the user to perform the exercise in a more precise way. In addition, as the output from the one or more sensors is not acquired by all the one or more sensors at once, whereas the output from the one or more sensors are acquired sequentially at every pre-defined time interval. Such an extraction reduces sheer complexity in designing of the sensor matrix. Also, as the power to the one or more sensors are supplied sequentially, the overall consumption of the power by the system is less which also makes the system less expensive and more reliable.

Further, the posture of the user while performing the at least one exercise may be determined more accurately and precisely without depending on an external camera such as Kinect™ and IR based cameras. Thereby enabling a non-intrusive way of determining the posture of the user while performing the at least one exercise on the mat.

While specific language has been used to describe the disclosure, any limitations arising on account of the same are not intended. As would be apparent to a person skilled in the art, various working modifications may be made to the method in order to implement the inventive concept as taught herein.

The figures and the foregoing description give examples of embodiments. Those skilled in the art will appreciate that one or more of the described elements may well be combined into a single functional element. Alternatively, certain elements may be split into multiple functional elements. Elements from one embodiment may be added to another embodiment. For example, order of processes described herein may be changed and are not limited to the manner described herein. Moreover, the actions of any flow diagram need not be implemented in the order shown; nor do all of the acts need to be necessarily performed. Also, those acts that are not dependant on other acts may be performed in parallel with the other acts. The scope of embodiments is by no means limited by these specific examples.

What is claimed is:

1. A system (10) to monitor an exercise posture of a user comprising:
   a mat (20) communicatively coupled to at least one wearable device (30) worn by the user at an upper body of the user, wherein the mat (20) is configured to allow the user to perform at least one exercise;
   at least one sensor matrix (40) located on one of a top of the mat (20) and within the mat (20), wherein each of the at least one sensor matrix (40) comprises one or more sensors (50), wherein the one or more sensors (50) is configured to generate an electrical signal upon making a contact of at least one part of a body of the user with the mat (20) while performing the at least one exercise on the mat (20);
   a plurality of sensor lines (60);
   a plurality of power lines (70), wherein the plurality of sensor lines (60) and the plurality of power lines (70) are in a pre-defined ratio;
   a processing subsystem (80) electrically coupled to the at least one sensor matrix (40), wherein the processing subsystem (80) comprises:
   a data acquisition module (90) configured to:
      extract a first set of data from at least one of the one or more sensors (50) through the plurality of sensor lines (60) at every pre-defined time interval sequentially;
      extract a second set of data from the at least one wearable device (30), wherein the second set of data is a representative of the at least one exercise performed by the user;
   a data processing module (100) operatively coupled to the data acquisition module (90), and configured to:
      process the first set of data and the second set of data using a processing technique;
      concatenate the first set of data and the second set of data to get a final set of data;
      compare the final set of data with a pre-defined set of posture data; and
      determine the posture of the at least one exercise performed by the user on the mat (20) based on a compared result.

2. The system (10) as claimed in claim 1, wherein the mat (20) comprises one of a Pilates mat, a yoga mat, a fitness mat and a wellness mat.

3. The system (10) as claimed in claim 1, wherein the processing sub system
   (80) further comprises a representation module operatively coupled to the data processing module (100), and configured to represent the posture of the at least one exercise performed by the user in at least one of a two-dimensional image and a three-dimensional image.

4. The system (10) as claimed in claim 3, wherein the processing subsystem (80) further comprises a posture detection module operatively coupled to the representation module, and configured to:
   determine the posture of the at least one exercise of the user from at least one of the two-dimensional image and the three-dimensional image using a computer vision technique; and
   generate a recommendation associated with the posture of the at least one exercise of the user based on a determined posture.

5. A method (250) for monitoring an exercise posture of a user comprising:
   generating, by at least one sensor matrix containing one or more sensors, an electrical signal upon making a contact of at least one part of a body of the user with a mat while performing at least one exercise on the mat; (260)
   extracting, by a data acquisition module, a first set of data from at least one of the one or more sensors through a corresponding plurality of sensor lines at every pre-defined time interval sequentially, the first set of data representing the contact of the at least one part of the body of the user with the mat; (270)
   extracting, by the data acquisition module, a second set of data from a wearable device, wherein the second set of data is representative of the at least one exercise performed by the user; (280)
   processing, by a data processing module, the first set of data and the second set of data using a processing technique; (290)
   concatenating, by the data processing module, the first set of data and the second set of data for getting a final set of data; (300)
   comparing, by the data processing module, the final set of data with a pre-defined set of posture data; and (310)
   determining, by the data processing module, the posture of the at least one exercise performed by the user on the mat based on a compared result (320).

6. The method (250) as claimed in claim 5, further comprising representing, by a representation module, the posture of the at least one exercise performed by the user in at least one of a two-dimensional image and a three-dimensional image.

7. The method (250) as claimed in claim 6, further comprising:
   determining, by a posture detection module, the posture of the at least one exercise of the user from at least one of the two-dimensional image and the three-dimensional image using a computer vision technique; and
   generating, by the posture detection module, a recommendation associated with the posture of the at least one exercise of the user based on a determined posture.

* * * * *